US00PP15132P3

(12) United States Plant Patent
Trees

(10) Patent No.: US PP15,132 P2
(45) Date of Patent: Sep. 7, 2004

(54) SUTERA PLANT NAMED 'BALABWHITI'

(50) Latin Name: *Sutera cordata*
Varietal Denomination: Balabwhiti

(75) Inventor: Scott C. Trees, Arroyo Grande, CA (US)

(73) Assignee: Ball FloraPlant, a division Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/329,637

(22) Filed: Dec. 26, 2002

(65) Prior Publication Data

US 2004/0128725 P1 Jul. 1, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—June Hwu
(74) *Attorney, Agent, or Firm*—Wood, Phillips, Katz, Clark & Mortimer

(57) ABSTRACT

A new and distinct Sutera plant named 'Balabwhiti', characterized by its white flowers, spreading, trailing habit, and medium green leaves.

2 Drawing Sheets

Latin name of the genus and species of plant claimed: *Sutera cordata.*

Variety denomination: 'Balabwhiti'.

BACKGROUND OF THE INVENTION

The present invention comprises a new and distinct Sutera plant, botanically known as *Sutera cordata,* and hereinafter referred to by the name 'Balabwhiti'.

'Balabwhiti' is the result of open pollination, with the female parent being a proprietary breeding selection designated BRD-019 (not patented). The new cultivar was discovered by the inventor during January 2001, in a controlled environment at Arroyo Grande, Calif.

Asexual reproduction of the new cultivar has been carried out at Arroyo Grande, Calif. and West Chicago, Ill. by terminal tip cuttings and has demonstrated that the characteristics of the new cultivar as herein described are firmly fixed and retained through successive generations of such asexual propagation.

SUMMARY OF THE INVENTION

It was found that the cultivar of the present invention:

(a) exhibits white flowers, (b) forms medium green foliage, (c) exhibits a basal branching character, and (d) exhibits a spreading and trailing growth habit.

The new cultivar of the present invention can be compared to 'Bridal Showers' (not patented). In side-by-side comparisons, plants of the new cultivar are taller, wider and have longer branches than 'Bridal Showers'. Additionally, plants of the new cultivar differ from plants of the female parent primarily in flower size.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown for 10 weeks in a greenhouse at West Chicago, Ill.

DETAILED BOTANICAL DESCRIPTION

Figure 1:
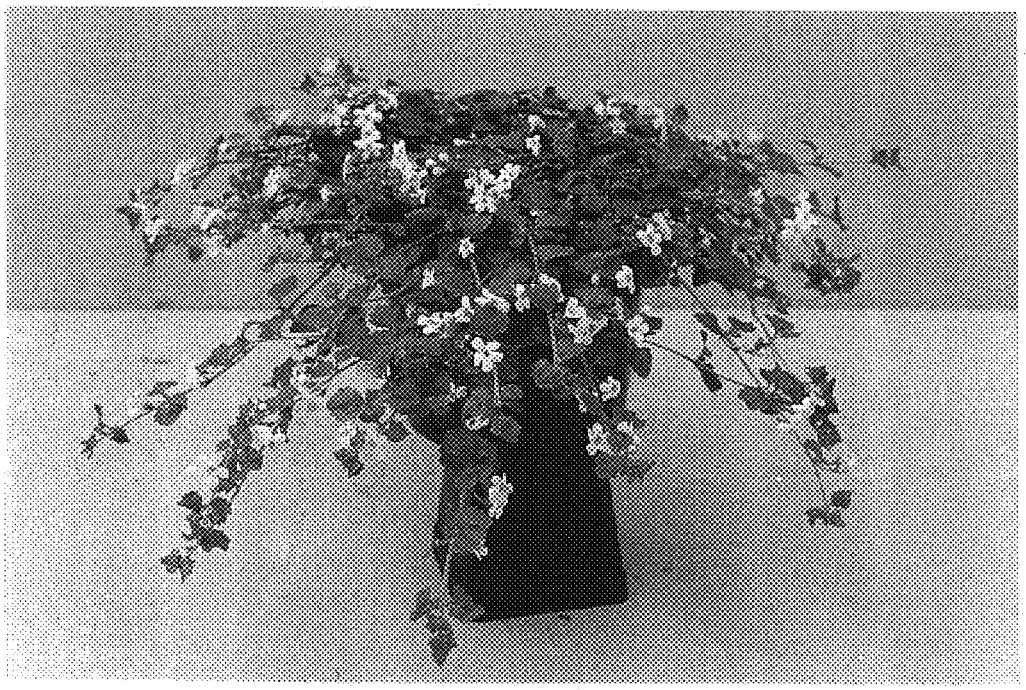
FIG. 1 illustrates the overall growth habit of the new cultivar.
Figure 2:
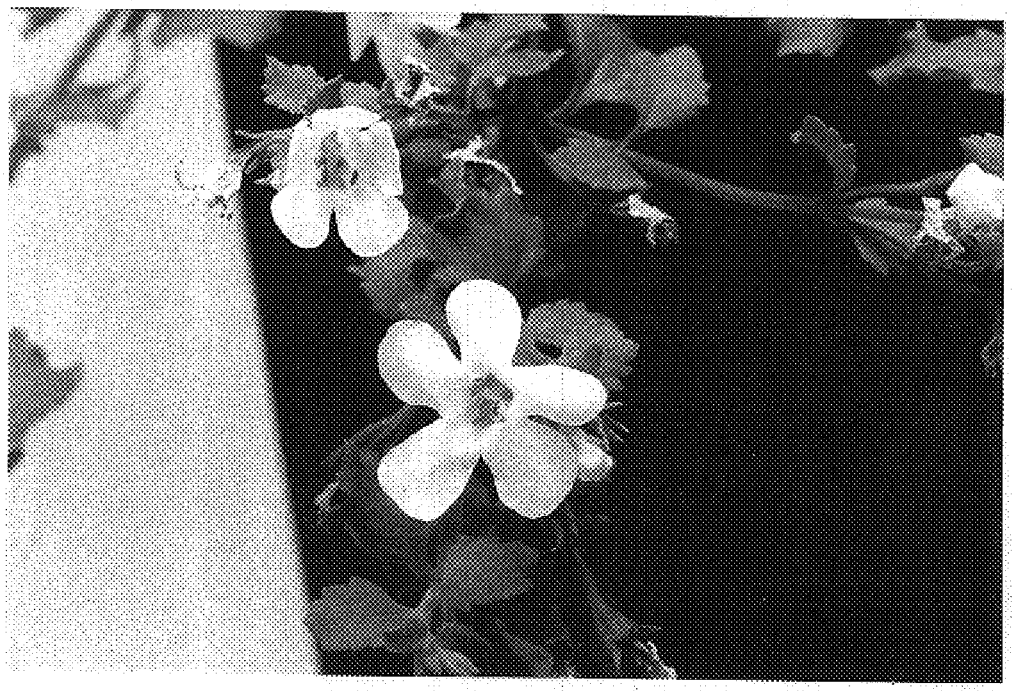
FIG. 2 illustrates a close-up view of foliage and an individual flower of the new cultivar.

'Balabwhiti' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 29, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown utilizing a soilless growth medium and maintaining temperatures of approximately 65° to 75° F. (18° to 24° C.) during the day and approximately 55° to 60° F. (13° to 15° C.) during the night and light levels of 4,000 and 8,000 footcandles. Plants used for the following descriptions and measurements were grown in 10 cm pots for 9 weeks from rooted cuttings.

Classification:

*Botanical.*—*Sutera cordata,* cultivar 'Balabwhiti'.

Parentage:

*Female parent.*—Proprietary breeding selection designated BRD-019.

Propagation:

*Type cutting.*—Terminal tip.

*Time to initiate roots.*—Approximately 7 to 10 days.

*Time to develop roots.*—Approximately 14 to 21 days.

*Root description.*—Fibrous, branching.

Plant description:

*Type.*—Annual.

*Habit of growth.*—Moderately vigorous with good basal branching. Pinching improves basal branching. A mature plant, 9 weeks after the planting of a rooted cutting, commonly measures approximately 6.3 cm in height and approximately 41.7 cm in diameter with an average of 3.8 primary branches.

*Form.*—Spreading and trailing.

*Primary branch.*—Length: Approximately 43.3 cm. Diameter: Approximately 1.6 mm. Texture: Very densely pubescent. Color: Lower surface is 146B, upper surface is 187A. Internode length at middle of branch: Approximately 3.3 cm.

*Foliage.*—Fragrance: Pungent. Form: Simple. Arrangement: Opposite, at an acute angle to the stem. Shape: Deltoid. Margin: Serrate. Apex: Acute. Base: Truncate. Upper surface is sparsely pubescent, lower surface has moderate pubescence along veins. Leaf length: Approximately 1.3 cm. Leaf width at widest point: Approximately 1.3 cm. Color: Upper surface of mature foliage is 137A; lower surface of mature foliage is 137C. Both upper and lower surfaces have pinnate venation closest to 143C. Petiole length: Approximately 4 mm. Petiole diameter: Approximately 1 mm. Petiole color: 137A.

Flowering description:

*Flowering habit.*—Freely flowering.

*Natural flowering season.*—Year round in greenhouse environment and spring through autumn in outdoor garden.

*Lastingness of bloom.*—Approximately 4 days.

*Flower type.*—Salverform, solitary. Flowers are persistent.

*Peduncle.*—Strong, with dense pubescence, at an acute angle to the stem, approximately 8 mm in length and less than 1 mm in diameter. Peduncle color is 144B.

*Bud.*—Shape: Ovoid. Length: Approximately 1 cm. Diameter: Approximately 3 mm. Color is 1D.

*Flower description.*—Flowers consist of five petals fused at base to form tube. Flower diameter: Approximately 1.6 cm. Petal shape: Obovate. Petal margin: Entire. Petal apex: Rounded. Petal texture: Glabrous. Lobe length: Approximately 6 mm. Lobe width: Approximately 5 mm. Lobe color: Upper and lower surfaces: Closest to 155D. Tube length: Approximately 1 cm. Tube diameter: Approximately 5 mm. Tube inner surface (throat): Texture: Moderately pubescent. Color: 17A. Tube outer surface: Texture: Moderately pubescent. Color: 2D at base, 21D at flower.

*Calyx.*—Shape: Tubular. Formed by five sepals, approximately 4 mm in length. Sepals are linear less than 1 mm in width, have an acute apex and entire margin. The both surfaces are densely pubescent and 146B.

*Reproductive organs.*—Androecium: There are 4 stamens which extrude from corolla tube. Anthers are 1 mm in length. Pollen is abundant and color is 14B. Gynoecium: One pistil, 1.1 cm in length. Stigma length: Approximately 2 mm. Stigma color: 144C. Style length: Approximately 8 mm. Style color: N144D. Ovary diameter: 1.5 mm. Ovary color: N144C.

Seed production: Seed production has not been observed.

Disease resistance: Resistance to pathogens has not been observed.

Hardiness zone: 'Balabwhiti' is hardy in zones nine (9) and above.

I claim:

1. A new and distinct Sutera plant named 'Balabwhiti' substantially as herein shown and described, which:

(a) exhibits white flowers, (b) forms medium green foliage, (c) exhibits a good basal branching character, and (d) exhibits a spreading and trailing growth habit.

* * * * *